US009596998B2

(12) United States Patent
Muehlsteff et al.

(10) Patent No.: US 9,596,998 B2
(45) Date of Patent: Mar. 21, 2017

(54) BALLISTOCARDIOGRAPHIC SENSOR SYSTEM WITH A SENSOR ARRANGEMENT AND METHOD OF BALLISTOCARDIOGRAPHIC DETECTION OF BODY MOVEMENTS

(75) Inventors: Jens Muehlsteff, Aachen (DE); Andreas Brauers, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1923 days.

(21) Appl. No.: 12/527,559

(22) PCT Filed: Feb. 18, 2008

(86) PCT No.: PCT/IB2008/050582
§ 371 (c)(1),
(2), (4) Date: Aug. 18, 2009

(87) PCT Pub. No.: WO2008/102298
PCT Pub. Date: Aug. 28, 2008

(65) Prior Publication Data
US 2010/0016685 A1    Jan. 21, 2010

(30) Foreign Application Priority Data
Feb. 22, 2007  (EP) .................................. 07102861

(51) Int. Cl.
A61B 5/103      (2006.01)
A61B 5/117      (2016.01)
(Continued)

(52) U.S. Cl.
CPC ........ *A61B 5/02444* (2013.01); *A61B 5/1102* (2013.01); *A61B 5/113* (2013.01); *A61B 5/6887* (2013.01); *A61B 5/6891* (2013.01); *A61B 5/0205* (2013.01); *A61B 5/0816* (2013.01); *A61B 5/6892* (2013.01); *A61B 5/721* (2013.01); *A61B 5/7264* (2013.01); *A61B 2560/0247* (2013.01); *A61B 2562/046* (2013.01)

(58) Field of Classification Search
CPC ... A61B 5/0205; A61B 5/0816; A61B 5/1102; A61B 5/113; A61B 5/6887; A61B 5/6892; A61B 5/7264; A61B 5/721
USPC ........ 600/481, 483, 484, 529, 534, 587, 595
See application file for complete search history.

(56) References Cited

U.S. PATENT DOCUMENTS 4,679,569 A * 7/1987 Lee ...................... A61B 5/1102
128/870
4,889,130 A * 12/1989 Lee ............................... 600/483
(Continued)

FOREIGN PATENT DOCUMENTS

JP  2004089267  3/2004
JP  2005095408  4/2005
(Continued)

*Primary Examiner* — Devin Henson

(57) ABSTRACT

Sensor arrangement, comprising at least one ballistocardiographic sensor for detecting body movements of a subject and at least one noise sensor for detecting vibration, method of ballistocardiographic detection of body movements, ballistocardiographic sensor system and uses of the sensor arrangement. It is suggested to pickup an external noise signal using an inertia sensor that is vibration isolated from a subject under ballistocardiographic examination.

16 Claims, 4 Drawing Sheets

(51) Int. Cl.
*A61B 5/024* (2006.01)
*A61B 5/11* (2006.01)
*A61B 5/113* (2006.01)
A61B 5/08 (2006.01)
A61B 5/00 (2006.01)
A61B 5/0205 (2006.01)

(56) References Cited

U.S. PATENT DOCUMENTS

| | | | |
|---|---|---|---|
| 6,315,740 B1* | 11/2001 | Singh | 600/595 |
| 6,558,351 B1 | 5/2003 | Steil et al. | |
| 2003/0233034 A1* | 12/2003 | Varri et al. | 600/301 |
| 2003/0236474 A1* | 12/2003 | Singh | A61B 5/1126 600/595 |
| 2006/0122525 A1* | 6/2006 | Shusterman | A61B 5/04007 600/513 |
| 2008/0077020 A1* | 3/2008 | Young | A61B 5/0205 600/484 |

FOREIGN PATENT DOCUMENTS

| | | |
|---|---|---|
| JP | 2005253924 | 9/2005 |
| WO | 2005074379 A2 | 8/2005 |
| WO | 2006088280 A1 | 8/2006 |

\* cited by examiner

BALLISTOCARDIOGRAPHIC SENSOR SYSTEM WITH A SENSOR ARRANGEMENT AND METHOD OF BALLISTOCARDIOGRAPHIC DETECTION OF BODY MOVEMENTS

The present invention relates to a sensor arrangement, a method of ballistocardiographic detection of body movements, a ballistocardiographic sensor system and uses of the sensor arrangement.

Ballistocardiography is a technique of detecting movements of a body of a subject which are imparted by ballistic forces associated with cardiac contraction and ejection of blood and with the deceleration of blood flow through the large blood vessels. Ballistocardiography is used for measuring a heart rate and respiration rate of a subject in a comfortable and unobtrusive way. The mechanical forces to be detected are small and therefore very sensitive pressure sensors are utilised which are attached to the subject's body. For example, the subject sits on a sensor or lies on a sensor in a bed. From the patent application publication US 2003/0233034 A1, a measurement of body internal movements (e.g. blood flow) by sensors integrated into furniture is known. An apparatus for measuring the vital functions of a patient is disclosed, which apparatus comprises a measuring chair, which measuring chair further comprises measuring sensors for measuring vital functions of the patient sitting in the measuring chair, in a non-invasive manner from the outside of the patient's body.

According to the described measurement principle the sensors are necessarily highly sensitive and thus are often jammed by environmental mechanical vibrations and motions caused, for example, by persons or pets, moving nearby the chair or bed, machines running close to the bed, or cars, tram, lorries passing by the building. In particular, in environments like hospitals or care institutions vibrations are produced by other persons moving in the vicinity of the bed or by machines like pumps and perfusors. These vibrations and therefore the induced signals are typically stronger than the desired signal of the body movements. It is a drawback that ballistocardiographic measurements which are superimposed by environmental noise are not analysable.

It is therefore an objective of the present invention to provide a sensor arrangement and method which allow a substantial increase of time, in which information from the ballistocardiographic measurements can be extracted.

The above mentioned objective is accomplished by a sensor arrangement, comprising at least one ballistocardiographic sensor for detecting body movements of a subject and at least one noise sensor for detecting vibration, wherein the noise sensor is vibration isolated from the body.

It is an advantage of the sensor arrangement according to the invention, that vibrations which are not induced by body movements are detectable by the noise sensor. Any kind of vibration which is not induced by body movements of the subject, are further referred to in here as noise vibration. The noise sensor detects a substantially pure noise vibration signal, further referred to as the noise signal, which is not superimposed with a signal induced by the body movements. By analysing the substantially undisturbed noise signal, it is advantageously possible to exactly discriminate passages of a ballistocardiographic signal from the ballistocardiographic sensor which are jammed by the noise signal from those passages which are unspoiled and thus allow an analysis. Furthermore, a reconstruction of at least a part of the jammed ballistocardiographic signal is advantageously possible on the basis of the undisturbed noise signal.

According to the present invention, the subject is a human or animal whose body allows for a measurement of vital functions. The body movements, in the sense of the invention, are imparted, for example, by ballistic forces (recoil and impact), associated with cardiac contraction and ejection of blood and with the deceleration of blood flow through the large blood vessels. Ballistocardiographic measurements comprise the measurement of force effects by the cardiac function on the body. When the heart pumps blood into the aorta and the pulmonary artery, the body is subjected to a recoil force in the direction opposite to the blood flow, the magnitude and the direction of the recoil force changing with the functional phase of the heart. This recoil force is measured by the ballistocardiographic sensor outside the body. Further, breathing and other movements of the subject contribute to the body movements.

The noise sensor according to the invention is vibration isolated from the body. Vibration isolated, in the sense of the invention, means that a signal induced by vibrations and/or movements of the body of the subject, which is detected by the noise sensor is substantially weaker than the signal detected by the ballistocardiographic sensor. For example, a signal strength of the noise signal induced by vibrations and/or movements of the body is less than 50% of the signal strength of the ballistocardiographic signal induced by the same vibrations and/or movements of the body, preferably less than 10%, more preferably less than 1% and most preferably less than 0.1%. The noise sensor is preferably a seismic sensor with a seismic mass, which may also be referred to as an inertial or ballistic sensor.

The arrangement according to the invention is advantageously utilisable for measuring, for example, a heart rate, a respiration rate, an activity or a blood pressure of a subject situated in a bed or chair. The ballistocardiographic sensor is preferably a sensitive pressure sensor which is coupled to the subject's body. For example, the subject might sit or rest on the ballistocardiographic sensor.

According to a preferred embodiment, the ballistocardiographic sensor is arranged at a structure, the structure supporting the body of the subject. In particular, the ballistocardiographic sensor is integrated into the structure. The structure may be any kind of furniture, for example, a bed, a chair or a wheelchair. More sensitive ballistocardiographic sensors and/or transducers advantageously enable the measurement of body internal movements, like e.g. blood flow, even if the sensor is integrated into the structure.

According to the invention, it is also preferred that the noise sensor is arranged in close proximity to the ballistocardiographic sensor and/or to a structure, which structure the ballistocardiographic sensor is arranged at. Furthermore preferred, the noise sensor and the ballistocardiographic sensor are arranged such that vibrations which do not result from the body movements of the subject are detected by both the noise sensor and the ballistocardiographic sensor. Locating the noise sensor near the ballistocardiographic sensor advantageously provides that the noise vibration is detected substantially equally by the noise sensor and the ballistocardiographic sensor. Advantageously, the substantial difference between the detected noise signal and the detected ballistocardiographic signal is the signal induced by body movements of the subject. Thus, in the sense of the invention, to arrange the noise sensor in close proximity to the ballistocardiographic sensor means to arrange the noise sensor in such a place where the noise vibration is detected substantially equally by the noise sensor and the ballistocardiographic sensor, i.e. the noise signal strength induced by the noise vibration is preferably at least 50% of the ballistocardiographic signal strength induced by the noise vibration. Generally, it depends on the environment how close the noise sensor is placed to the ballistocardiographic sensor. Preferably, the noise sensor is arranged on the ground or building floor. In particular, the noise sensor is arranged at a floor, upon which a structure for supporting the body stands. It may be adequate to arrange the noise sensor in the same room as the ballistocardiographic sensor. More preferably, the noise sensor is arranged in the vicinity of the structure, for example, under the bed or chair. This advantageously provides analysable noise signals even in strongly frequented environments, like, for example, hospital rooms with several beds.

According to the invention, it is furthermore preferred that the noise sensor is movably attached to a structure supporting the body of the subject. For example, in the case of a home bed which is typically not moved very often, the noise sensor may just be placed nearby the bed statically. In a professional care environment or for a hospital bed, however, it is advantageous that the noise sensor is mobile, for example as a part of the bed. The person skilled in the art recognises the noise sensor is yet mechanically decoupled from the rest of the bed, to provide the vibration isolation.

According to the invention, it is furthermore preferred that the structure comprises a mounting, the mounting being adapted to protrude the noise sensor from the structure. The mounting, in the sense of the invention, is any kind of link connecting the structure and the noise sensor which advantageously allows to retract the sensor, e.g. for relocation of the structure, and to protrude the sensor to the designated position for detection of the noise vibration.

According to the invention, it is furthermore preferred that the structure comprises an undercarriage and a fixing brake, the mounting being operationally connected to the brake such that the noise sensor is protruded upon the fixing brake being applied. Advantageously, the noise sensor is automatically protruded to the designated position upon the brake of the structure being applied. The hospital personnel, for example, thus does not need to apply the noise sensor manually. Operationally connected, in the sense of the embodiment, includes any mechanical gearing or mechatronic kind of actuation.

Another object of the present invention is a method of ballistocardiographic detection of body movements of a subject, comprising the steps of detecting a ballistocardiographic signal from the body of the subject, and detecting a noise signal, wherein the noise signal is detected by a noise sensor, the noise sensor being vibration isolated from the body of the subject.

It is an advantage of the method according to the invention, that noise vibrations are detectable by the noise sensor. The noise sensor detects a noise signal, which is not superimposed with the ballistocardiographic signal.

In a preferred embodiment, the noise signal is used for dejamming the ballistocardiographic signal and/or for an evaluation of the ballistocardiographic signal. By analysing the noise signal, it is advantageously possible to exactly discriminate passages of a ballistocardiographic signal which are jammed by the noise vibration from those passages which are unspoiled and thus allow an analysis. A reconstruction of at least a part of the jammed ballistocardiographic signal advantageously provides the ability to analyse even parts of the ballistocardiographic signal which are superimposed by noise vibrations on the basis of the noise signal.

In a more preferred embodiment, noise cancellation filter techniques for the dejamming of the ballistocardiographic signal are used. Even more preferable, an adaptive filter is used, wherein the filter is advantageously adapted using the noise signal. For example, if a ballistocardiographic signal is corrupted by a noise vibration the frequency of the noise vibration might wander. A static filter could excessively degrade the quality of the ballistocardiographic signal, since the latter likely comprises frequency components in the range rejected by the static filter. The adaptive filter advantageously takes input both from the ballistocardiographic signal and from the noise signal and is thus able to track the actual frequency of the noise as it fluctuates. Such an adaptive technique advantageously allows for a filter with a smaller rejection range, which increases the quality of the filtered signal. Furthermore preferred, fuzzy logic techniques for the dejamming of the ballistocardiographic signal are used.

In a further preferred embodiment, a spectrum of the noise signal is subtracted from a signal power spectrum of the ballistocardiographic signal and a dejammed signal is restored, preferably by an inverse Fourier transformation. The spectrum of the noise signal is preferably gained by a fast Fourier transformation (FFT) analysis of the noise signal. The method according to this embodiment is advantageously effective and is easy to implement.

Another object of the present invention is a ballistocardiographic sensor system with a sensor arrangement according to the invention, which system further comprises a data processing unit for processing signals from the noise sensor and the ballistocardiographic sensor, wherein the processing is carried out according to the method according to the invention. The data processing unit may advantageously be, for example, any computer with an appropriate interface for the input of the noise signal and the bcg signal.

Another object of the present invention is a use of a sensor arrangement according to the invention for monitoring one or more of heart rate, a blood pressure, a respiration rate and activity of a subject.

Another object of the present invention is a use of a sensor arrangement according to the invention for surveillance of a person, in particular in a care environment.

Another object of the present invention is a use of a sensor arrangement according to the invention for monitoring arrhythmia.

Another object of the present invention is a use of a sensor arrangement according to the invention for sleep quality assessment.

Another object of the present invention is a use of a sensor arrangement according to the invention for surveillance of congestive heart failure patients.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

FIG. 1 schematically illustrates a structure for attachment of ballistocardiographic sensors according to the prior art.

Figure 1:
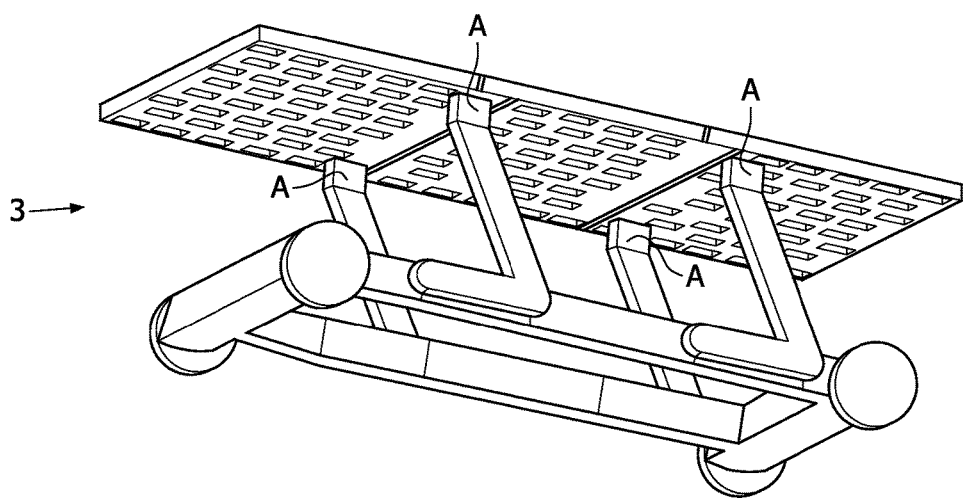

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn true to scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

In FIG. 1, a structure 3 is depicted on which a sensor arrangement (not shown) may be arranged. Here, a typical bed is shown, as it is found in a hospital. The positions A denote preferred positions for ballistocardiographic sensors (not shown).

Figure 2A:
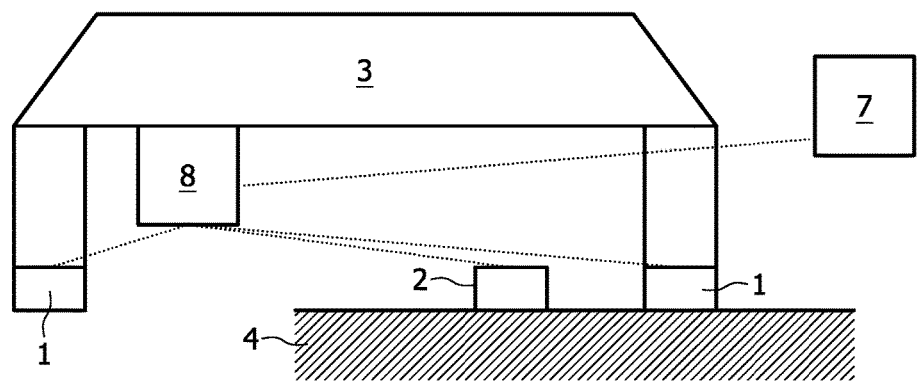
FIGS. 2a and 2b illustrate embodiments of a sensor arrangement and a ballistocardiographic sensor system according to the invention.
Figure 2B:
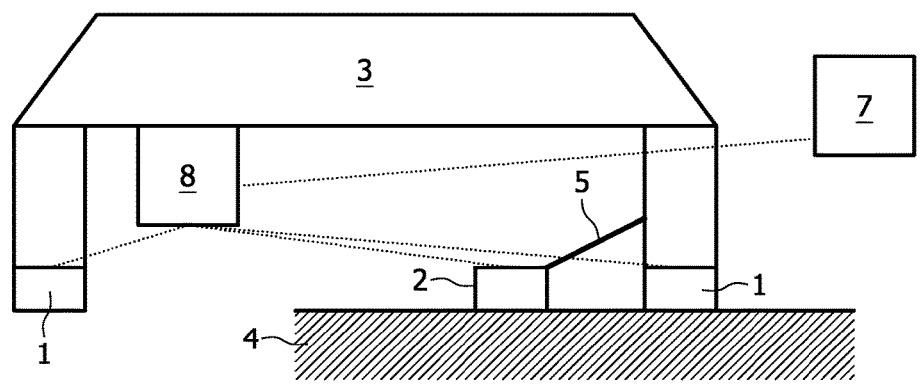

In FIGS. 2a and 2b, embodiments of the sensor arrangement and the ballistocardiographic sensor system according to the invention are illustrated schematically. The structure 3 may be, for example, a bed or a chair. Ballistocardiographic sensors are arranged at the structure 3 to detect body movements of a subject (not depicted) who is situated on the structure 3. The structure 3 is standing on a floor 4 of a room, for example. According to the invention, the sensor arrangement comprises a noise sensor 2 which is vibration isolated from the body of the subject. The noise sensor 2 is preferably a seismic sensor with a seismic mass. The response of the noise sensor 2 to external impulses has to be calibrated against the response of the structure 3 to the same impulse. This is preferably done regularly, i.e. during typical measurement cycles due to the effect of the subjects weight or other mechanical changes to the structure 3 on the mechanical response of the system.

In FIG. 2a, the noise sensor is placed on the floor 4. A transmission of vibration from the structure 3 and thus from the subject to the noise sensor 2 is effectively prevented, as vibrations induced by body movements of the subject are comparably weak. Noise vibrations, however, which are, for example, induced by steps of a person walking on the floor 4, are advantageously detected by the noise sensor 2. In FIG. 2b, an embodiment of the sensor arrangement at the structure 3 is depicted, which is advantageous for mobile structures 3 as, for example, a wheeled bed in a hospital. The noise sensor 2 is attached to the structure via a mounting 5. The person skilled in the art recognises, that the mounting 5 is adapted not to transmit vibrations from the structure 3 to the noise sensor 2, i.e. the noise sensor 2 is nevertheless vibration isolated from the structure 3. Preferably, the mounting 5 is retractable to transfer the noise sensor 2 from the depicted working position to a deployment position. Furthermore, the mounting 5 may be operationally connected to a brake of the wheels (not depicted) of the bed, such that the noise sensor 2 is automatically lowered to the floor 4 upon application of the brake. The sensor arrangement as depicted in FIGS. 2a and 2b form a part of a ballistocardiographic system according to the invention which further comprises a data processing unit 7 with an interface (not depicted) for the input of a noise signal (FIG. 3) from the noise sensor 2 and a ballistocardiographic signal (FIG. 3) from the ballistocardiographic sensors 1. The signals may be amplified and/or converted by transducers 8. Connections from the noise sensor 2 and/or the ballistocardiographic sensors 1 to the data processing unit may comprises wired connections or wireless communication lines.

Figure 3:
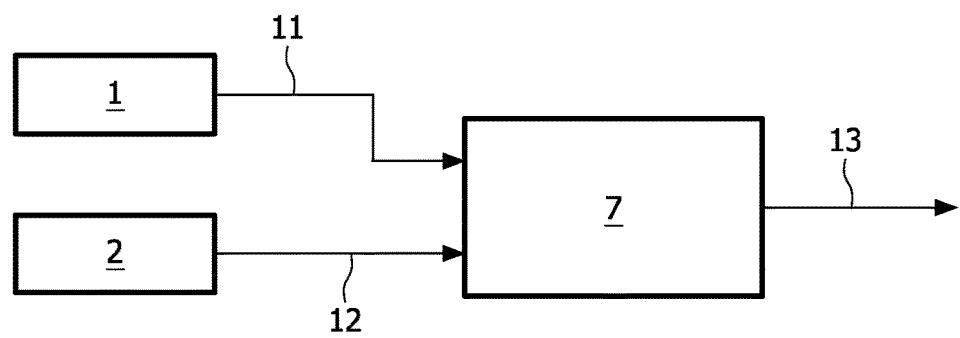
FIG. 3 shows a schematic diagram which illustrates the sensor arrangement and method of ballistocardiographic detection according to the invention.

In FIG. 3, the sensor arrangement and method of ballistocardiographic detection according to the invention is illustrated in a schematic diagram. A noise vibration jammed ballistocardiographic signal 11 from the ballistocardiographic sensor 1 and a noise signal 12 from the noise sensor 2 are fed into the data processing unit 7, where the noise signal 12 is used to subtract the jamming noise vibration from the ballistocardiographic signal 11. An output signal 13 is a dejammed ballistocardiographic signal which is advantageously analysable.

Figure 4:
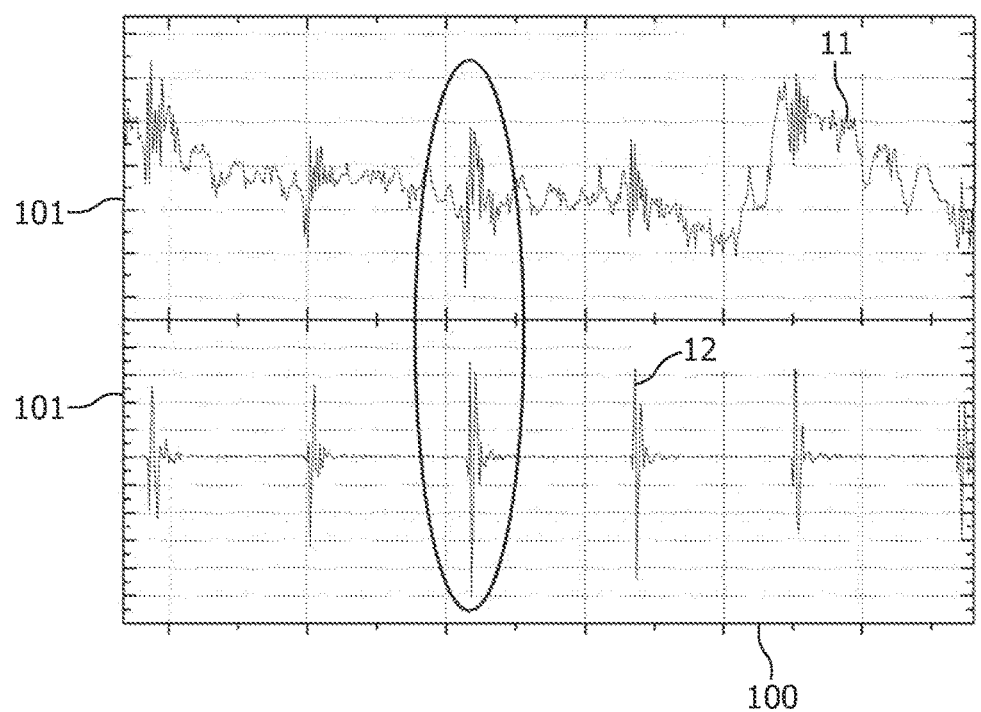
FIG. 4 shows an example of a ballistocardiographic signal and a noise signal from a ballistocardiographic sensor and a noise sensor.

In FIG. 4, an example of the ballistocardiographic signal 11 and the noise signal 12 from the ballistocardiographic sensor 1 and the noise sensor 2 which only records a seismic noise is given. Time is given on axis 100 and the signal on the respective axes 101. The ballistocardiographic signal 11 is from a subject lying in a bed with breathing movements and heart movements visible in the trace. The ballistocardiographic signal 11, however, is perturbed by movements of another person walking close to the bed which may happen frequently in hospital and care environments. The single steps of the walking person are clearly visible in the noise signal 12 of the noise sensor 2. Movements by the subject only show up in the ballistocardiographic signal 11 and not in the noise signal 12. Due to the vibration isolation of the noise sensor 2, the two sources of the ballistocardiographic signal 11 can be discriminated. Environmental noise can be analysed and to a significant extent eliminated from the ballistocardiographic signal 11.

The invention claimed is:

1. A sensor arrangement, comprising:
   at least one ballistocardiographic sensor configured to detect body movements of a subject;
   a structure configured to support a body of the subject;
   at least one noise sensor configured to detect vibration; and
   a mechanical mounting affixed to the structure, the mounting being configured to:
      vibrationally isolate the noise sensor from the body,
      protrude the noise sensor from the structure to a working position, and
      retract the noise sensor to a stowed position.

2. The sensor arrangement according to claim 1, wherein the ballistocardiographic sensor is arranged at the structure.

3. The sensor arrangement according to claim 1, wherein the noise sensor is a seismic sensor which is arranged in close proximity to the ballistocardiographic sensor and/or to the structure.

4. The sensor arrangement according to claim 1, wherein the noise sensor and the ballistocardiographic sensor are arranged such that vibrations which do not result from the body movements of the subject are detected by both the noise sensor and the ballistocardiographic sensor.

5. A ballistocardiographic sensor system comprising:
the sensor arrangement according to claim 1; and
a data processor configured to process signals from the noise sensor and the ballistocardiographic sensor.

6. The sensor arrangement according to claim 1, wherein said sensor arrangement is configured for monitoring one or more of heart rate, respiration rate and activity of a subject.

7. The sensor arrangement according to claim 1, wherein said sensor arrangement is configured for surveillance of a person in a care environment.

8. The sensor arrangement according to claim 1, wherein said sensor arrangement is configured for monitoring arrhythmia.

9. The sensor arrangement according to claim 1, wherein said sensor arrangement is configured for assessing sleep quality.

10. The sensor arrangement according to claim 1, wherein said sensor arrangement is configured for surveillance of congestive heart failure patients.

11. A sensor arrangement comprising:
at least one ballistocardiographic sensor for detecting body movements of a subject;
a structure supporting a body of the subject, the structure including an undercarriage and a fixing brake;
a mechanical mounting affixed to the structure; and
at least one noise sensor movably attached to the structure via the mechanical mounting for detecting vibration;
wherein the noise sensor is vibrationally isolated from the body, and wherein the mechanical mounting is operationally connected to the brake such that the noise sensor is protruded from the structure upon the fixing brake being applied.

12. A method of ballistocardiographic detection of body movements of a subject, comprising:
detecting a ballistocardiographic signal from the body of the subject with a ballistocardiographic sensor,
with a mounting, mechanically protruding a noise sensor from a structure that supports the body of the subject to a working position and retracting the noise sensor to a deployed position, and
detecting a noise signal by the noise sensor,
wherein the noise sensor is vibrationally isolated from the body of the subject.

13. The method according to claim 12, wherein the noise signal is used for dejamming the ballistocardiographic signal and/or for an evaluation of the ballistocardiographic signal.

14. The method according to claim 12, further comprising:
noise cancellation filtering the ballistocardiographic signal.

15. The method according to claim 12, further comprising:
protruding the noise sensor to the working position in response to applying a brake to fix a position of an undercarriage of the support.

16. The method according to claim 12, further including:
subtracting a spectrum of the noise signal from a spectrum of the ballistocardiographic signal; and
restoring a dejammed signal.

* * * * *